(12) United States Patent
Hill

(10) Patent No.: US 9,213,341 B2
(45) Date of Patent: Dec. 15, 2015

(54) BIOLOGICAL SAFETY CABINET WITH A FALLING-FILM EVAPORATOR

(71) Applicant: American Sterilizer Company, Mentor, OH (US)

(72) Inventor: Aaron L. Hill, Madison, OH (US)

(73) Assignee: AMERICAN STERILIZER COMPANY, Mentor, OH (US)

( * ) Notice: Subject to any disclaimer, the term of this patent is extended or adjusted under 35 U.S.C. 154(b) by 611 days.

(21) Appl. No.: 13/650,506

(22) Filed: Oct. 12, 2012

(65) Prior Publication Data

US 2014/0105785 A1    Apr. 17, 2014

(51) Int. Cl.
| | |
|---|---|
| *A61L 2/20* | (2006.01) |
| *G05D 21/02* | (2006.01) |
| *A61L 9/00* | (2006.01) |
| *G05D 9/12* | (2006.01) |
| *G05D 23/19* | (2006.01) |

(52) U.S. Cl.
CPC . *G05D 21/02* (2013.01); *A61L 2/20* (2013.01); *A61L 2/208* (2013.01); *A61L 9/00* (2013.01); *G05D 9/12* (2013.01); *G05D 23/19* (2013.01); *A61L 2202/11* (2013.01); *A61L 2202/18* (2013.01)

(58) Field of Classification Search
CPC ............. A61L 2/00; A61L 2/20; A61L 2/208; A61L 9/00; A61L 9/02; A61L 9/03; A61L 9/032; A61L 2202/11; A61L 2202/122; A61L 2202/14; A61L 2202/18; A61L 2202/182
See application file for complete search history.

(56) References Cited

U.S. PATENT DOCUMENTS

| | | | |
|---|---|---|---|
| 2,751,338 A | 6/1956 | Schwemberger | 202/63 |
| 4,909,999 A | 3/1990 | Cummings et al. | 422/298 |
| 6,780,288 B1 | 8/2004 | Bloomfield et al. | 203/12 |

(Continued)

FOREIGN PATENT DOCUMENTS

| | | | | |
|---|---|---|---|---|
| DE | 87 12 317.7 | 3/1988 | | A61L 2/20 |
| EP | 0 774 263 A1 | 5/1997 | | A61L 2/20 |

OTHER PUBLICATIONS

International Search Report (ISR) and Written Opinion issued by the International Searching Authority (ISA) in connection with corresponding PCT/US13/52657, dated Dec. 6, 2013.

(Continued)

*Primary Examiner* — Timothy Cleveland
(74) *Attorney, Agent, or Firm* — Kusner & Jaffe; Michael A. Centanni

(57) ABSTRACT

A method for decontaminating a biological safety cabinet with a falling film evaporator. The method includes the steps of:
providing a falling-film evaporator within a cavity of a biological safety cabinet, the evaporator having a housing defining a cavity and an evaporation element is disposed in the cavity;
conveying a liquid decontaminant from a source of liquid decontaminant to the evaporation element such that the liquid decontaminant flows along a surface of the evaporation element;
conveying a carrier gas through the cavity of the housing wherein the carrier gas is conveyed along the surface of the evaporation element to evaporate the liquid decontaminant thereby forming a mixture of the carrier gas and the vaporized decontaminant; and
exhausting the mixture into the cavity of the biological safety cabinet to decontaminate articles and surfaces in the cavity.

12 Claims, 5 Drawing Sheets

(56) References Cited

U.S. PATENT DOCUMENTS

| | | | |
|---|---|---|---|
| 7,790,104 B2 | 9/2010 | Adams et al. | 422/29 |
| 7,919,059 B2 | 4/2011 | Hill | 422/298 |
| 2007/0053813 A1* | 3/2007 | Martin | 422/295 |
| 2007/0274858 A1 | 11/2007 | Childers et al. | 422/28 |
| 2008/0105282 A1 | 5/2008 | Fernholz et al. | 134/26 |
| 2009/0217626 A1 | 9/2009 | Kemp et al. | 53/407 |
| 2010/0252066 A1 | 10/2010 | Kaiser | 134/1 |
| 2011/0076189 A1 | 3/2011 | McVey et al. | 422/28 |
| 2011/0079503 A1 | 4/2011 | Heins et al. | 203/7 |
| 2011/0176959 A1 | 7/2011 | Ko | 422/33 |

OTHER PUBLICATIONS

"Falling film evaporator," Wikipedia, pp. 1-2, http://en.wikipedia.org/wiki/Falling_film_evaporator, last accessed Oct. 4, 2011.

"Biosafety cabinet," Wikipedia, pp. 1-4, http://en.wikipedia.org/wiki/Biosafety_cabinet, prior to Jun. 11, 2012.

BioGen™—M Dry Vapour Hydrogen Peroxide Generator—Mini, Technical Data Sheet, 2 pp., Howorth Bio Technology Ltd., Bolton, UK, prior to May 4, 2012.

* cited by examiner

BIOLOGICAL SAFETY CABINET WITH A FALLING-FILM EVAPORATOR

FIELD OF THE INVENTION

The present invention relates generally to the art of decontamination, and more particularly to a method and apparatus for decontaminating a biological safety cabinet ("BSC").

BACKGROUND OF THE INVENTION

A biological safety cabinet (also referred to as a "biosafety cabinet" or a "microbiological safety cabinet") is an enclosed, ventilated laboratory workspace that is used for working safely with articles contaminated with (or potentially contaminated with) pathogens. The primary purpose of a BSC is to serve as a primary means to protect a laboratory worker and the surrounding environment from pathogens.

In general, a BSC includes a chamber for receiving an article. An opening is provided for allowing an individual to access the interior of the chamber. In some embodiments, a door is movable relative to the opening for sealing and unsealing the opening. In other embodiments, gloves are permanently attached to the opening to isolate a user and the surrounding environment from the interior of the chamber while still allowing the user to manipulate the articles in the chamber. One type of BSC is designed such that air is drawn from the chamber of the BSC, passed through a HEPA-filter to remove harmful bacteria and viruses from the air and is returned to the chamber.

It is known to use formaldehyde to decontaminate the BSC between uses in order to reduce the likelihood that pathogens from one article will be passed to other articles during subsequent uses of the BSC. After a BSC is exposed to formaldehyde, the formaldehyde is eliminated, or decomposed, using ammonia bicarbonate. However, ammonia bicarbonate produces a solid residue that must be removed from the cabinet by manual wiping. As such, a user must access the interior of the BSC and manually wipe all the surfaces in the BSC to remove the solid residue. Moreover, formaldehyde is considered a carcinogen. As such, it is desirable to limit the exposure of a user to formaldehyde.

The present invention provides a biological safety cabinet that includes a falling-film evaporator for generating vaporized hydrogen peroxide (VHP) to quickly and safely decontaminate the biological safety cabinet.

SUMMARY OF THE INVENTION

In accordance with an embodiment of the present invention, there is provided a method for decontaminating a biological safety cabinet with a falling film evaporator. The method includes the steps of:
  providing a falling-film evaporator within a cavity of a biological safety cabinet, the evaporator having a housing defining a cavity with an evaporation element disposed in the cavity;
  conveying a liquid decontaminant from a source of liquid decontaminant to the evaporation element such that the liquid decontaminant flows along a surface of the evaporation element;
    conveying a carrier gas through the cavity of the housing wherein the carrier gas is conveyed along the surface of the evaporation element to evaporate the liquid decontaminant thereby forming a mixture of the carrier gas and the vaporized decontaminant; and
    exhausting the mixture into the cavity of the biological safety cabinet to decontaminate articles and surfaces in the cavity.

In accordance with another aspect of the present invention, there is provided a falling-film evaporator for generating a vaporized decontaminant. The evaporator includes a housing that defines a cavity. A source of a liquid decontaminant is fluidly connected to the cavity of the housing. An evaporation element is disposed in the cavity of the housing. The evaporation element has at least one surface for receiving the liquid decontaminant. A pump conveys the liquid decontaminant from the source to the surface of the evaporation element wherein the liquid decontaminant flows along the surface of the evaporation element. A fan draws a carrier gas from the chamber and conveys the carrier gas through the cavity of the housing wherein the carrier gas flows along the surface of the evaporation element to evaporate the liquid decontaminant thereby forming a vaporized decontaminant.

An advantage of the present invention is the provision of a falling-film evaporator that is disposed within a biological safety cabinet to decontaminate the interior of the biological safety cabinet.

Another advantage of the present invention is the provision of a falling-film evaporator that utilizes vaporized hydrogen peroxide to decontaminate the interior of a biological safety cabinet.

Another advantage of the present invention is the provision of a falling-film evaporator that does not require formaldehyde to decontaminate a biological safety cabinet.

Another advantage of the present invention is the provision of a falling-film evaporator that does not require that an individual manually wipe the interior surfaces of a biological safety cabinet after a decontamination process.

Another advantage of the present invention is the provision of a falling-film evaporator that produces vaporized hydrogen peroxide in a low cost manner, Still another advantage of the present invention is the provision of a falling-film evaporator, as described above, wherein the vaporized hydrogen peroxide is generated using heated air.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
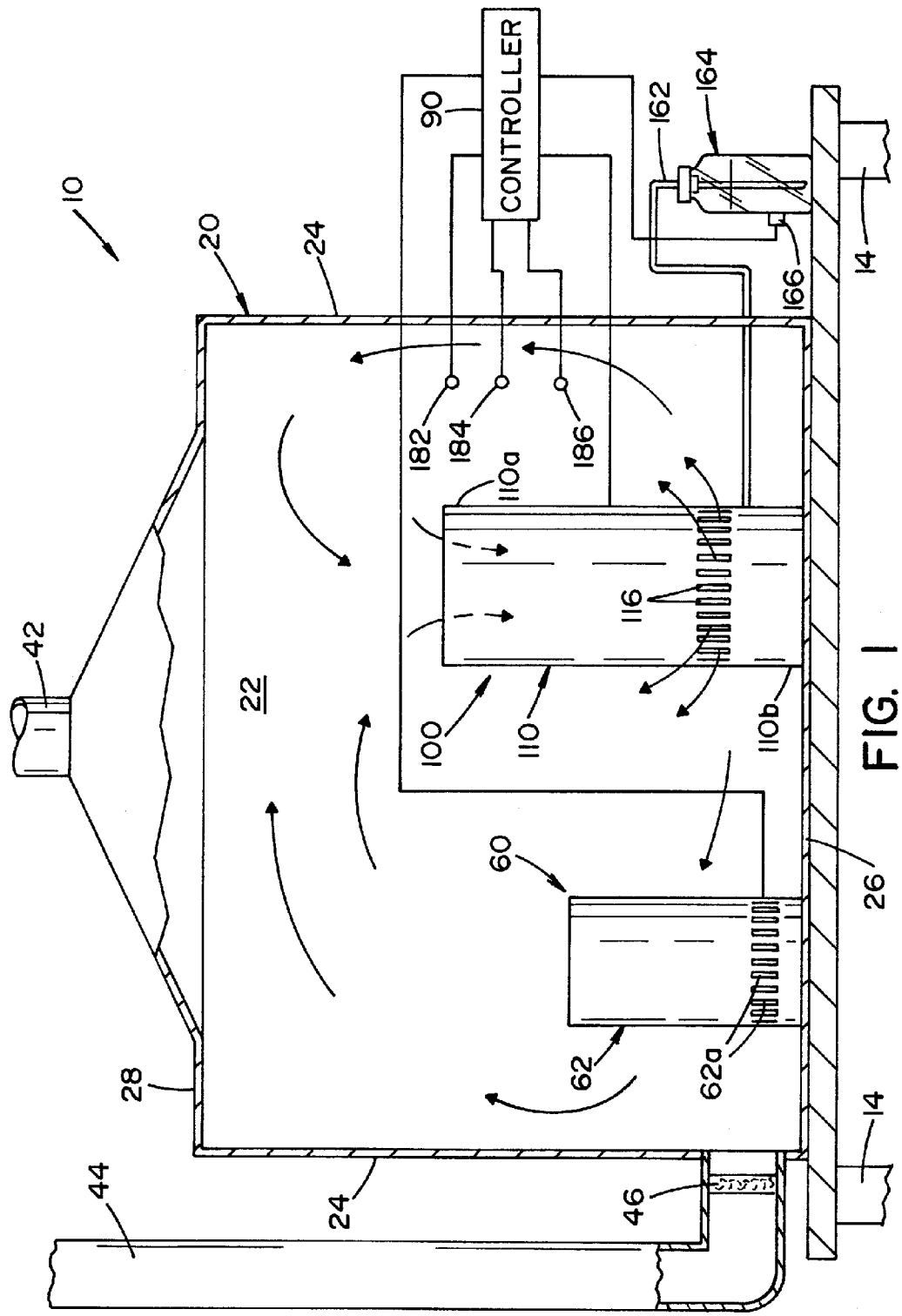
FIG. 1 is a partially-sectioned view of a biological safety cabinet with a falling-film evaporator disposed therein illustrating air flow during a conditioning phase and a decontamination phase, according to a preferred embodiment of the present invention.

Referring now to the drawings wherein the showings are for the purpose of illustrating a preferred embodiment of the invention only, and not for the purpose of limiting the same, FIG. 1 shows a biological safety cabinet ("BSC") 10 for safely working with articles in a controlled environment.

Cabinet 10 includes a housing 20 that defines a chamber or region 22. Housing 20 includes side walls 24, a bottom wall 26 and a top wall 28. Top wall 28 is formed to define a sloped hood of housing 20. Legs 14 support cabinet 10 above a floor (not shown).

An exhaust conduit 42 connects to top wall 28 of housing 20 to fluidly connect chamber 22 to a blower (not shown). The blower draws air from chamber 22 through exhaust conduit 42.

A return conduit 44 fluidly connects a lower portion of chamber 22 to the surrounding environment to allow make-up air to be drawn into chamber 22 through return conduit 44. A filter 46 is disposed in return conduit 44 for removing harmful bacteria and viruses from the air drawn into chamber 22. Filter 46 is preferably a "high efficiency particulate air" (HEPA) filter. It is contemplated that return conduit 44 may be connected to an output of the blower in exhaust conduit 42 such that all or a portion of the air removed from chamber 22 is returned to chamber 22.

Figure 2:
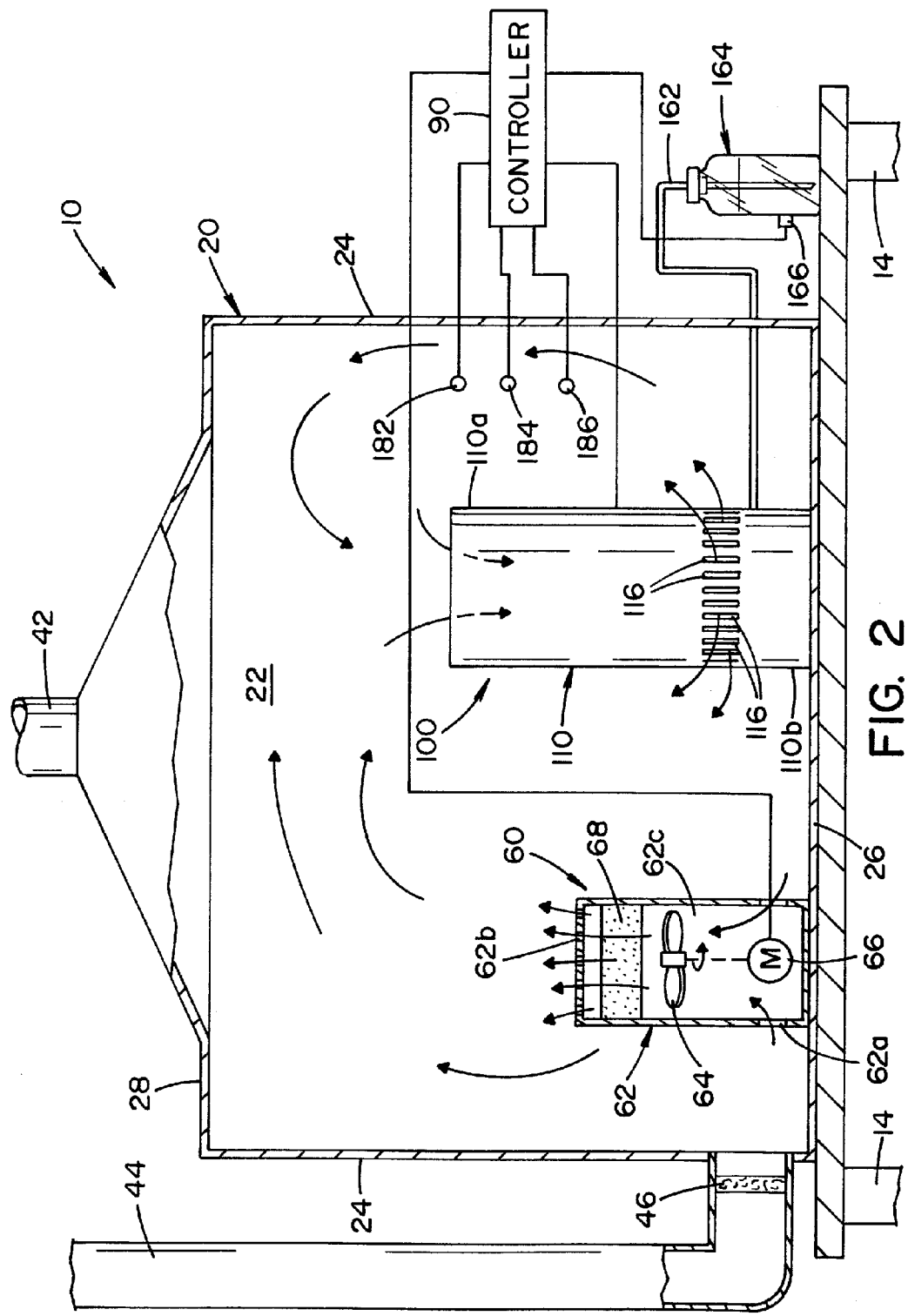
FIG. 2 is a partially-sectioned view of the biological safety cabinet shown in FIG. 1, illustrating air flow during an aeration phase.

Referring now to FIG. 2, a destroyer 60 is provided for conveying the air in chamber 22 through a catalytic converter 68 during an aeration phase of a decontamination cycle (discussed in detail below). Destroyer 60 includes a housing 62, a fan 64 and catalytic converter 68. Housing 62 is an elongated, cylindrically-shaped element that is vertically oriented in chamber 22. Housing 62 includes inlet openings 62a at a lower end thereof and outlet openings 62b at an upper end thereof. Housing 62 defines a passageway 62c therethrough that extends between inlet openings 62a and outlet openings 62b.

Fan 64, driven by a motor 66, is disposed in housing 62 for conveying air along passageway 62c of housing 62 from inlet openings 62a to outlet openings 62b. Motor 66 is connected to a controller 90. Controller 90 controls the operation of motor 66, as shall be described in detail below.

Catalytic converter 68 is provided for deactivating a vaporized decontaminant conveyed along passageway 62c of housing 62. Catalytic converter 68 is disposed in housing 62 at a location downstream of fan 64. In a preferred embodiment, the vaporized decontaminant is vaporized hydrogen peroxide ($H_2O_2$) and catalytic converter 68 is operable to destroy hydrogen peroxide in air flowing therethrough. More specifically, catalytic converter 68 converts hydrogen peroxide into water ($H_2O$) and oxygen ($O_2$), as is conventionally known.

Controller 90 includes a microprocessor or microcontroller programmed to control the operation of cabinet 10. Controller 90 may include input means (e.g., a keypad or buttons) and output means (e.g., a display, a speaker and/or a printer).

Figure 3:
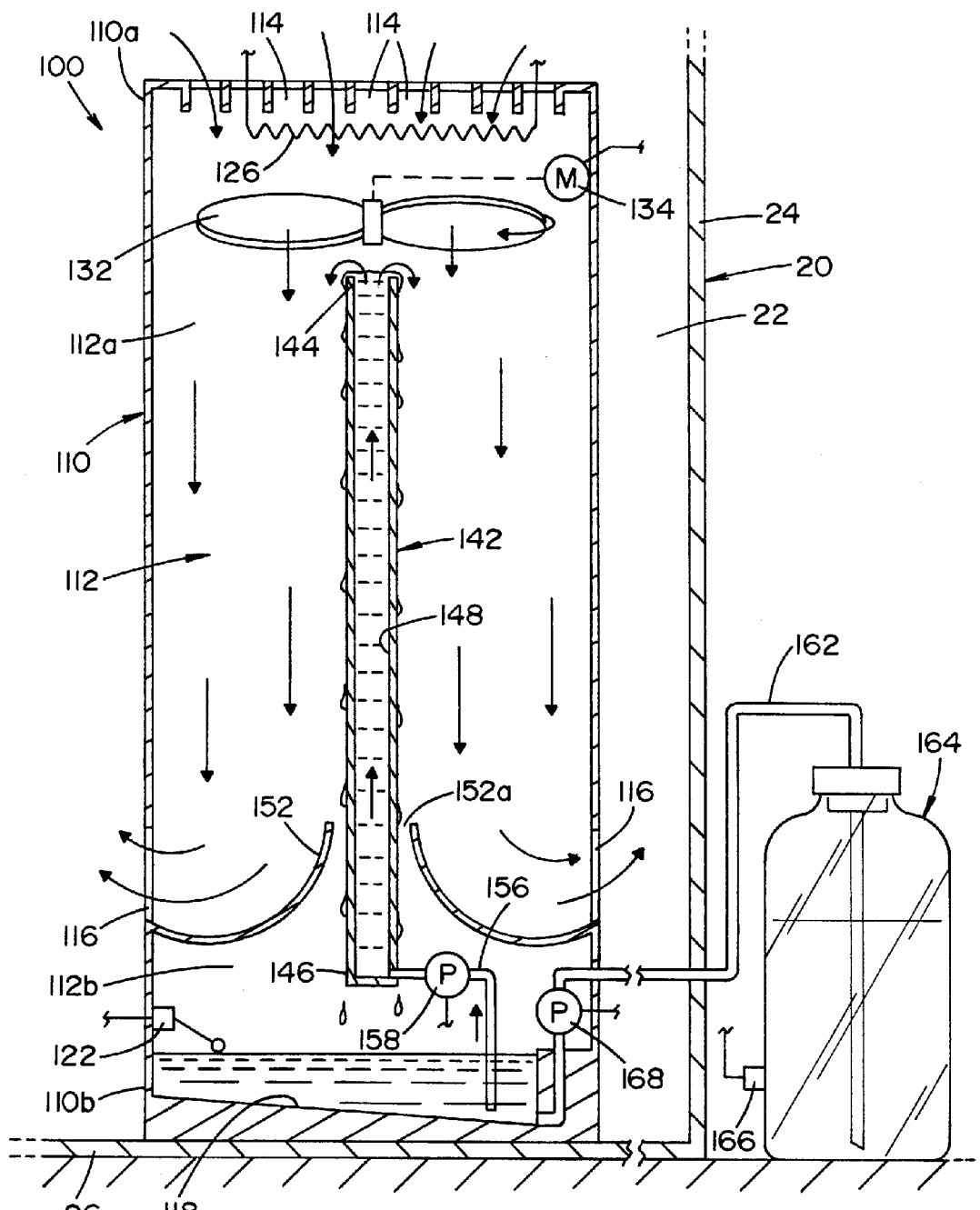
FIG. 3 is a sectional view of the falling-film evaporator shown in FIG. 1.

Referring now to FIG. 3, a falling-film evaporator 100, according to a preferred embodiment of the present invention, is shown. Evaporator 100 generally includes a housing 110, a fan 132, an evaporation element 142 and a liquid decontaminant reservoir 164. In a preferred embodiment, the liquid decontaminant is an aqueous solution of hydrogen peroxide (e.g., 35% to 59% hydrogen peroxide by weight).

Housing 110 is an elongated, cylindrically-shaped element that is vertically oriented in chamber 22. Housing 110 defines an internal cavity 112 therethrough. Housing 110 has an upper end 110a and a lower end 110b. A plurality of inlet openings 114 are formed in upper end 110a. Inlet openings 114 are dimensioned to hinder large debris from entering internal cavity 112 while allowing air to pass therethrough. In the embodiment shown, inlet openings 114 are formed in an end wall of housing 110. A plurality of outlet openings 116 are formed in lower end 110b. In the embodiment shown, outlet openings 116 are rectangular-shaped openings.

Lower end 110b of housing 110 is formed to define a sump 118. Sump 118 is dimensioned to hold a predetermined quantity of liquid decontaminant. A level sensor 122 is disposed near sump 118. Level sensor 122 provides a signal to controller 90 indicative of a predetermined level of liquid decontaminant in sump 118.

Fan 132, driven by a motor 134, is disposed in an upper portion of internal cavity 112 for drawing air into cavity 112. Fan 132 is designed to draw air into the upper portion of cavity 112 at a rate of between about 20 CFM and about 30 CFM. The foregoing rate is selected to provide the necessary number of air exchanges needed to evaporate liquid hydrogen peroxide in evaporator 100, as described in detail below. Fan 132 forces the air down through cavity 112 and out through outlet openings 116. It is contemplated that motor 134 is a variable speed motor for varying the rate of flow of air through cavity 112. Controller 90 is connected to motor 134 to control the operation thereof.

A heater 126 is disposed in cavity 112. In a preferred embodiment, heater 126 is disposed between inlet openings 114 and fan 132. Heater 126 is designed to heat the air conveyed through the upper portion of cavity 112. Controller 90 is connected to heater 126 to control the operation of heater 126. In the embodiment shown, heater 126 is an electrical resistance heating device.

Evaporation element 142 is disposed in cavity 112 at a location downstream of fan 132 and upstream of outlet openings 116. Evaporation element 142 is an elongated element that is vertically oriented in cavity 112. In the embodiment shown, evaporation element 142 is axially aligned with the axis of housing 110. Evaporation element 142 has an open upper end 144 and a closed lower end 146. Evaporation element 142 defines an internal cavity 148 for receiving the liquid decontaminant. In the embodiment shown, evaporation element 142 is cylindrical in shape.

A baffle 152 is disposed above sump 118. Baffle 152 divides cavity 112 into an upper evaporation chamber 112a and a lower storage chamber 112b. Baffle 152 is annular in shape with an opening 152a through a central portion thereof. In a preferred embodiment, baffle 152 is dimensioned and positioned such that a lower portion of evaporation element 142 extends through opening 152a of baffle 152. Opening 152a of baffle 152 and evaporation element 142 are dimensioned such that a small gap is formed therebetween. Baffle 152 is designed to direct the air conveyed through housing 110 into a predetermined direction, as described in detail below. In a preferred embodiment, baffle 152 has a curved upper surface.

A conduit 156 fluidly connects internal cavity 148 of evaporation element 142 to sump 118. A sump pump 158 is disposed in conduit 156 for conveying metered amounts of liquid decontaminant from sump 118 to internal cavity 148 of evaporation element 142. Controller 90 is connected to sump pump 158 for controlling the operation of sump pump 158.

Sump pump 158 may include an encoder (not shown) that allows monitoring of the amount of liquid decontaminant being metered to evaporation element 142.

A supply conduit 162 extends through side wall 24 of cabinet 10 and through housing 110. Supply conduit 162 fluidly connects sump 118 of housing 110 to liquid decontaminant reservoir 164. Liquid decontaminant reservoir 164 is designed to hold a predetermined quantity of liquid decontaminant. In a preferred embodiment, reservoir 164 is a bottle dimensioned to hold approximately three (3) gallons of aqueous liquid hydrogen peroxide. A level sensor 166 provides a signal indicative of a predetermined level of liquid decontaminant in reservoir 164 to controller 90. In a preferred embodiment, reservoir 164 is disposed outside of housing 20 to allow a user to easily access reservoir 164. It is contemplated that reservoir 164 may be disposed inside of housing 20 to minimize the distance between sump 118 and reservoir 164.

A supply pump 168 is disposed within supply conduit 162 for conveying the liquid decontaminant between reservoir 164 and sump 118 of housing 110. In a preferred embodiment, supply pump 168 is operable to convey the liquid decontaminant in both a first direction from reservoir 164 to sump 118 and a second direction from sump 118 back to reservoir 164. Controller 90 is connected to supply pump 168 for controlling the operation thereof. Supply pump 168 may include an encoder (not shown) that allows monitoring of the amount of liquid decontaminant being metered between reservoir 164 and sump 118. By way of example, and not limitation thereof, supply pump 168 may be a positive displacement pump, such as a piston pump or a peristaltic pump.

As shown in FIG. 1, a humidity sensor 182, a temperature sensor 184, and a hydrogen peroxide ($H_2O_2$) concentration sensor 186 are disposed within chamber 22. Humidity sensor 182 is operable to sense the relative humidity (RH) within chamber 22. Humidity sensor 182 provides an electrical signal to controller 90 indicative of the humidity in chamber 22.

Temperature sensor 184 is operable to sense the temperature within chamber 22. Temperature sensor 184 provides an electrical signal to controller 90 indicative of the temperature in chamber 22. Controller 90 is programmed such that the absolute humidity in chamber 22 may be determined from the relative humidity and temperature sensed respectively by humidity sensor 182 and temperature sensor 184. Alternatively, humidity sensor 182 can take the form of a sensor that directly measures absolute humidity.

Hydrogen peroxide concentration sensor 186 is a sensing device (e.g., an infrared sensor or electrochemical sensor), and is operable to sense the concentration of hydrogen peroxide within chamber 22. Hydrogen peroxide concentration sensor 186 provides an electrical signal to controller 90 indicative of the concentration of hydrogen peroxide in chamber 22.

As indicated above, the decontamination of cabinet 10 follows use of cabinet 10 by a user. The present invention shall now be further described with reference to the operation of cabinet 10 during a typical decontamination cycle. A typical decontamination cycle includes a conditioning phase, a decontamination phase and an aeration phase. Prior to running a decontamination cycle, reservoir 164 is filled with a liquid decontaminant. In addition, data regarding the percentage of hydrogen peroxide in the liquid decontaminant is input into controller 90. As noted above, in a preferred embodiment, a liquid decontaminant comprised of 35% to 59% hydrogen peroxide by weight is used. However, a liquid decontaminant having different concentrations of hydrogen peroxide is also contemplated.

When a decontamination cycle of cabinet 10 is initiated, controller 90 causes motor 134 to drive fan 132, thereby drawing air from chamber 22 into housing 110 of falling-film evaporator 100 through inlet openings 114. The air is then conveyed through cavity 112 and is exhausted out through outlet openings 116, as represented by arrows in FIGS. 1 and 3. Arrows in FIG. 1 represent the flow pattern developed within chamber 22 from the operation of fan 132. As illustrated in FIG. 3, baffle 152 directs that air conveyed through cavity 112 of housing 110 into a radially outward pattern away from housing 110 through outlet openings 116.

Air that is drawn into cavity 112 of housing 110 passes over heater 126 and evaporation element 142. During the decontamination cycle, controller 90 controls heater 126 to heat the air passing through cavity 112 and maintain a desired temperature within chamber 22 of cabinet 10, as described in detail below.

Controller 90 also activates supply pump 168 to convey metered amounts of the liquid decontaminant from decontaminant reservoir 164 to sump 118 of housing 110. Once the liquid decontaminant has reached a predetermined level in sump 118, as determined by level sensor 122, controller 90 activates sump pump 158 to convey metered amounts of the liquid decontaminant from sump 118 to internal cavity 148 of evaporation element 142. Internal cavity 148 fills with the liquid decontaminant and the liquid decontaminant overflows from open upper end 144 of evaporation element 142 (as represented by arrows in FIG. 3). The liquid decontaminant flows downwardly along the outer surface of evaporation element 142.

As represented by arrows in FIG. 3, air is forced downwardly over the outer surface of evaporation element 142. As the air flows over evaporation element 142, the liquid decontaminant on the outer surface of evaporation element 142 evaporates to form vaporized hydrogen peroxide (VHP) and water vapor. The VHP and water vapor are transported or carried by the flow of air out of cavity 112 of housing 110 through outlet openings 116. Any liquid decontaminant on the outer surface of evaporation element 142 that does not evaporate in the air flows downwardly to the lower end 146 of evaporation element 142 and collects in sump 118.

It is believed that the flow rate of liquid decontaminant to evaporation element 142, the flow rate of the air over evaporation element 142 and the temperature of the air determine the evaporation rate of the liquid decontaminant on evaporation element 142. Controller 90 is programmed to maintain a desired evaporation rate of the liquid decontaminant by controlling sump pump 158, motor 134 and heater 126.

During the conditioning phase, hydrogen peroxide vapor is injected into chamber or region 22 at a relatively high rate to bring the concentration of hydrogen peroxide vapor up to a desired level in a relatively short period of time. The conditioning phase continues until the concentration of hydrogen peroxide vapor in chamber or region 22, as measured by hydrogen peroxide concentration sensor 186, is within a predetermined acceptable range.

After the conditioning phase, the decontamination phase of the decontamination cycle is initiated. During the decontamination phase, controller 90 controls motor 134, sump pump 158 and heater 126 to maintain the concentration of hydrogen peroxide vapor within chamber or region 22 within a user defined acceptable range. The user defined acceptable range is based on the concentration of hydrogen peroxide vapor required to decontaminate the surfaces of the BSC. The decontamination phase is run for a user determined period of time.

During the aforementioned conditioning and decontamination phases, controller 90 monitors level sensors 122, 166 to determine the level of the liquid decontaminant in sump 118 and reservoir 164. If level sensor 166 in reservoir 164 provides a signal to controller 90 indicative that the level of liquid decontaminant in reservoir 164 is low, controller 90 will sound an alarm to notify an operator that the level of liquid decontaminant in reservoir 164 is low. Controller 90 also monitors level sensor 122 in sump 118 to determine if the level of liquid decontaminant in sump 118 is too high. If the level of the liquid decontaminant in sump 118 is above a predetermined level, controller 90 will de-energize supply pump 168 so that liquid decontaminant from reservoir 164 ceases to flow into sump 118.

Throughout the respective operational phases, humidity sensor 182, temperature sensor 184, and hydrogen peroxide concentration sensor 186 respectively monitor the relative humidity (RH), temperature, and hydrogen peroxide concentration within chamber or region 22, and provide electrical signals to controller 90 indicative of the relative humidity, temperature, and hydrogen peroxide concentration. Based on the measured relative humidity (RH) and temperature, controller 90 calculates the absolute humidity (AH) in chamber 22. Alternatively, as described above, humidity sensor 182 may take the form of a sensor that directly measures absolute humidity.

Controller 90 is programmed to control the concentration of VHP in chamber 22 using one or more of the methods disclosed in U.S. patent application Ser. No. 11/741,069, entitled "Vaporized Hydrogen Peroxide Decontamination System with Concentration Adjustment Mode," now issued as U.S. Pat. No. 7,919,059, both of which are hereby incorporated herein by reference, U.S. patent application Ser. No. 11/741,069 discloses one method wherein a controller is programmed to provide "feedback control." Feedback control is used to prevent condensation of hydrogen peroxide within a chamber or region during a decontamination cycle, and to operate a system more efficiently to minimize the decontamination cycle time (i.e., the total time required to complete a successful decontamination cycle).

Similar to the controller disclosed in U.S. patent application Ser. No. 11/741,069, controller 90 of the present invention is programmed to maintain a desired evaporation rate of the liquid decontaminant by controlling sump pump 158, motor 134 and heater 126. The evaporation rate of the liquid decontaminant, in turn, determines the actual $H_2O_2$ concentration within region 22. Using the "feedback control" method disclosed in U.S. patent application Ser. No. 11/741,069, controller 90 is programmed to maintain the concentration of $H_2O_2$ within region 22 at a level that hinders condensation of hydrogen peroxide within chamber or region 22 during the decontamination cycle.

After the decontamination phase, controller 90 causes sump pump 158 to turn off, thereby ceasing the flow of liquid decontaminant to internal cavity 148 of evaporation element 142. It is contemplated that evaporation element 142 contains a small hole, i.e., a weep hole, (not shown) in a bottom thereof for allowing the liquid decontaminant in internal cavity 148 of evaporation element 142 to slowly drain therefrom. Controller 90 also causes supply pump 168 to draw liquid decontaminant from sump 118 to convey the liquid decontaminant back into reservoir 164. Supply pump 168 remains energized until all the liquid decontaminant in sump 118 is conveyed into reservoir 164.

Thereafter, the aeration phase, as illustrated in FIG. 2, is initiated to bring the concentration of hydrogen peroxide in chamber 22 down to an allowable threshold (e.g., about 1 ppm or less). Controller 90 causes motor 66 to drive fan 64, thereby drawing air and VHP from chamber 22 into housing 62. The VHP is conveyed along passageway 62c of housing 62 and through catalytic converter 68. As the VHP is conveyed through catalytic converter 68, the VHP is broken down by catalytic converter 68 into water ($H_2O$) and oxygen ($O_2$). Controller 90 also causes motor 134 to drive fan 132 during the aeration phase thereby drawing air from chamber 22 into cavity 112 of housing 110 of falling-film evaporator 100. Residual VHP and water vapor in cavity 112 are transported or carried by the flow of air out of housing 110 and into chamber 22 of cabinet 10. The residual VHP is then drawn by fan 64 into passageway 62c and is conveyed through catalytic converter 68 wherein the VHP is broken down. In this respect, controller 90 controls the operation of cabinet 10 during the aeration phase to reduce the concentration of hydrogen peroxide vapor to an allowable threshold.

The present invention provides a system that uses a vaporous hydrogen peroxide (VHP) to decontaminate a BSC. Use of VHP as a decontaminant does not require that a user manually wipe down the surfaces of the BSC after the decontamination process. The present invention evaporates a liquid decontaminant (e.g., hydrogen peroxide) by blowing heated air over a surface of an evaporation element whereon the liquid decontaminant is disposed. The liquid decontaminant evaporates and is transported or carried into the BSC to decontaminant the cabinet and articles therein. In addition, any liquid decontaminant remaining at the end of the decontamination cycle is safely returned to a storage reservoir for use during subsequent decontamination cycles. The present invention thus provides a falling-film evaporator for quickly and safely decontaminating a BSC.

Figure 4:
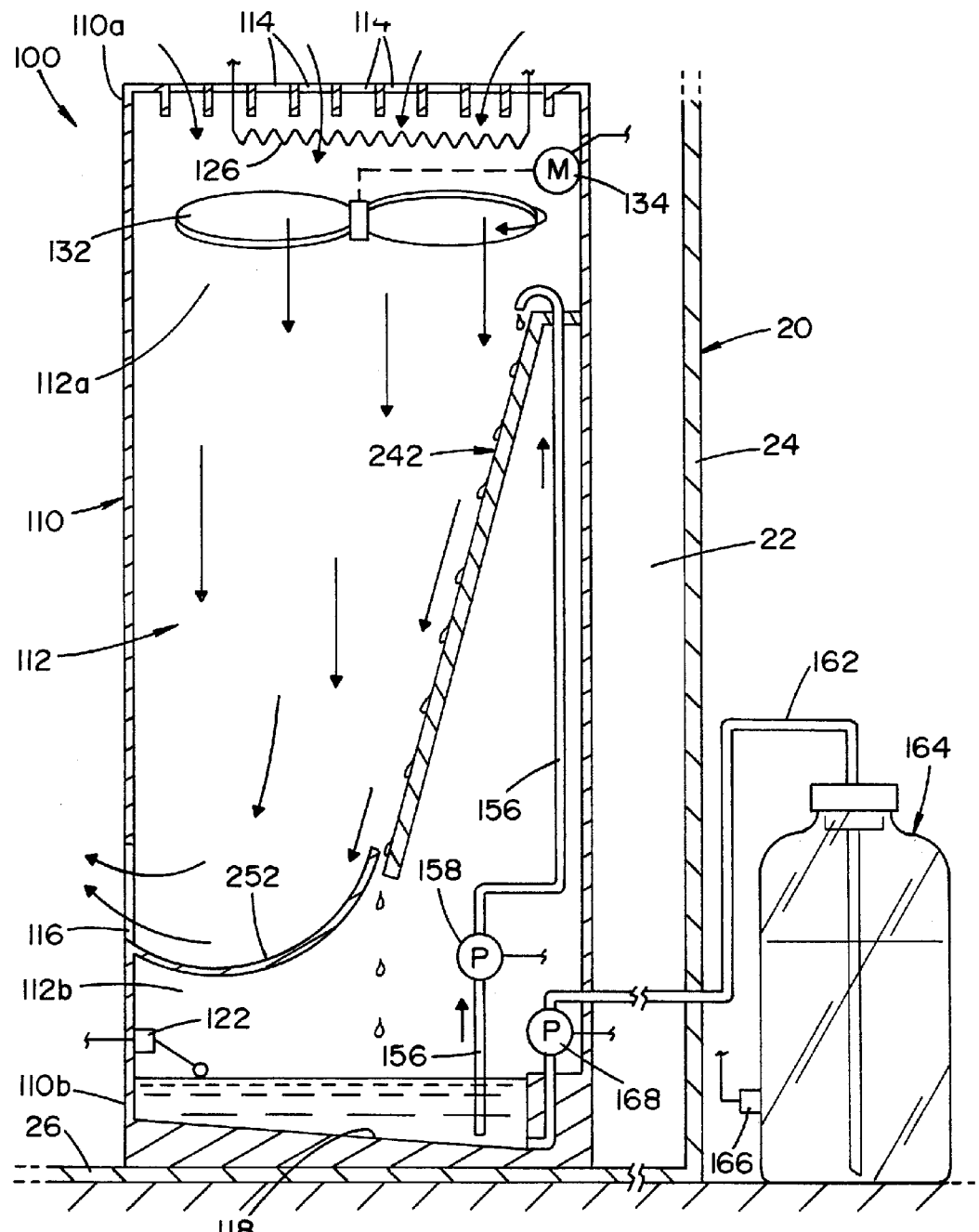
FIG. 4 is a sectional view of a falling-film evaporator illustrating another embodiment of the present invention.

According to another embodiment of the present invention, shown in FIG. 4, an evaporation element 242 is disposed in chamber 22 of housing 20. In the embodiment shown, evaporation element 242 is a flat plate that is disposed at an angle and located within chamber 22 of housing 20. A baffle 252 is disposed at a lower end of evaporation element 242 for directing the flow of air in a predetermined direction. During operation of the present embodiment, sump pump 158 conveys liquid decontaminant to an upper edge of evaporation element 242 and the liquid decontaminant flows downward along an upper surface of evaporation element 242. As air is blown over evaporation element 242, by fan 136, the liquid decontaminant evaporates to form vaporized hydrogen peroxide and water vapor. The VHP and water vapor are then transported into chamber 22 of cabinet 10. The remaining phases of operation of the present embodiment are similar to the first embodiment described in detail above.

Figure 5:
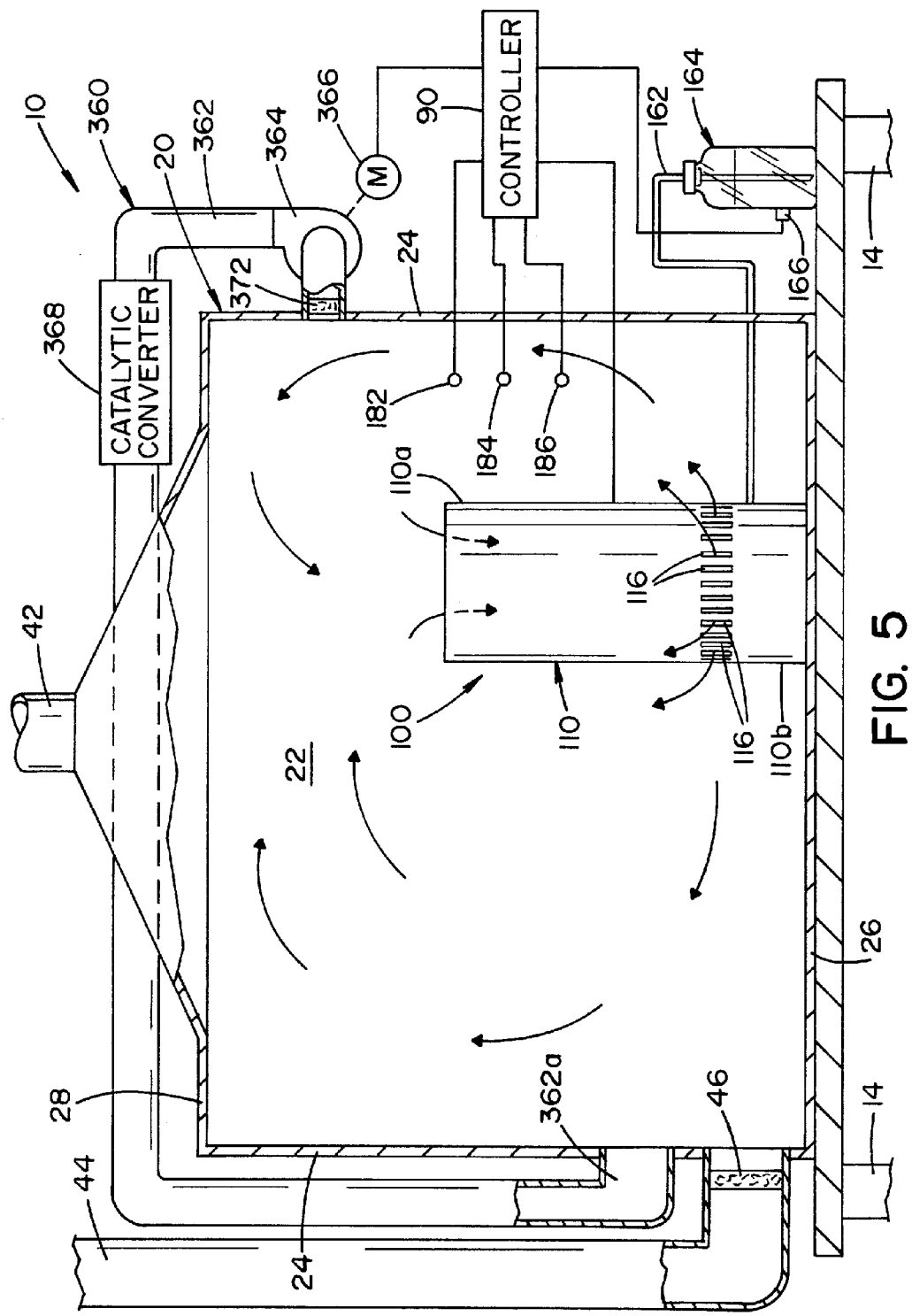
FIG. 5 is a partially-sectioned view of a biological safety cabinet with a falling-film evaporator disposed therein, according to yet another embodiment of the present invention.

In another embodiment of the present invention, shown in FIG. 5, cabinet 10 includes a circulation system 360 that is provided for conveying the air in chamber 22 through a catalytic converter 368 and back into chamber 22 during the aeration phase of the decontamination cycle (discussed in detail above). Circulation assembly 360 includes a conduit 362, a blower 364, catalytic converter 368 and a filter 372. Conduit 362 defines a passageway 362a therethrough. Passageway 362a of conduit 362 fluidly communicates with chamber 22 at both ends. In particular, one end of conduit 362 is connected to a lower portion of housing 20 and another end of conduit 362 is connected to an upper portion of housing 20. In the embodiment shown, conduit 362 extends through side walls 24 of housing 20. Blower 364, driven by a motor 366, is disposed within conduit 362 for conveying air along passageway 362a. Motor 366 is connected to controller 90. Controller 90 controls the operation of motor 366.

Catalytic converter 368 is provided for deactivating a vaporized decontaminant conveyed along passageway 362a of conduit 362. Catalytic converter 368 is disposed in conduit 362 at a location downstream of blower 364. Catalytic converter 368 is similar to catalytic converter 68, described in detail above.

Filter 372 is disposed in conduit 362 at a location upstream of blower 364. Filter 372 is provided for removing debris and dirt from air drawn into conduit 362 to protect blower 364 and catalytic converter 368 from damage. The operation of circulation system 360 during the aeration phase is similar to the above-described operation of destroyer 60 during the aeration phase.

It is also contemplated that in another embodiment of the present invention falling-film evaporator 100 may not include hydrogen peroxide concentration sensor 186. In this embodiment, controller 90 is programmed to run a predetermined cycle. The predetermined cycle uses the initial air temperature and humidity level, as measured by humidity sensor 182 and temperature sensor 184, and controls motor 134, pumps 158, 168 and heater 126 to inject a predetermined concentration of vaporized hydrogen peroxide into chamber or region 22. The predetermined concentration of vaporized hydrogen peroxide is selected to hinder or prevent condensation within chamber or region 22 during the decontamination cycle.

It is contemplated that the evaporation element of the present invention may take on other shapes and orientations within falling-film evaporator system 100 without altering from the spirit and scope of the invention. For example, the evaporation element may be a tubular element that is skewed at an angle in the housing or a cone-shape element wherein the liquid decontaminant flows downwardly from an apex of the cone to the base of the cone.

The foregoing description is a specific embodiment of the present invention. It should be appreciated that this embodiment is described for purposes of illustration only, and that numerous alterations and modifications may be practiced by those skilled in the art without departing from the spirit and scope of the invention.

Having described the invention, the following is claimed:

1. A method for decontaminating a biological safety cabinet with a falling film evaporator, the method comprising the steps of:
    providing the falling-film evaporator within a cavity of the biological safety cabinet, said evaporator having a housing defining a cavity, an evaporation element disposed in said cavity of said housing and a sump, said evaporation element having an upper end and a lower end and said sump disposed below said lower end of said evaporation element;
    conveying a liquid decontaminant from a source of liquid decontaminant to said upper end of said evaporation element such that said liquid decontaminant flows along a surface of said evaporation element from said upper end of said evaporation element to said lower end of said evaporation element;
    conveying a carrier gas through said cavity of said housing wherein said carrier gas is conveyed along said surface of said evaporation element to evaporate at least a portion of said liquid decontaminant, thereby forming a mixture of said carrier gas and said vaporized decontaminant;
    collecting a remaining portion of said liquid decontaminant in said sump and conveying said remaining portion of said liquid decontaminant to said upper end of said evaporation element; and
    exhausting said mixture into said cavity of said biological safety cabinet to decontaminate articles and surfaces in said cavity of said biological safety cabinet.

2. The method according to claim 1, including a step of:
    determining a concentration of said vaporized decontaminant using a decontaminant sensor, a temperature sensor and a humidity sensor.

3. The method according to claim 2, including a step of:
    controlling said concentration of said vaporized decontaminant by adjusting a rate that said liquid decontaminant is conveyed to said evaporation element.

4. The method according to claim 2, including a step of:
    controlling said concentration of said vaporized decontaminant by adjusting a rate that said carrier gas flows over said surface of said evaporation element.

5. The method according to claim 2, including a step of:
    providing a heater element for heating said carrier gas prior to said carrier gas flowing over said surface of said evaporation element.

6. The method according to claim 5, including a step of:
    controlling said concentration of said vaporized decontaminant by adjusting a temperature of said carrier gas flowing over said surface of said evaporation element.

7. The method according to claim 1, including a step of:
    providing a baffle in said housing for directing said carrier gas and said vaporized decontaminant in said housing in a predetermined direction away from said housing.

8. The method according to claim 1, wherein said evaporation element is a tube.

9. The method according to claim 1, wherein said evaporation element is a plate.

10. The method according to claim 1, wherein said evaporation element is disposed substantially vertically in said housing.

11. The method according to claim 1, wherein said liquid decontaminant is aqueous liquid hydrogen peroxide.

12. The method according to claim 1, wherein said carrier gas is conveyed in a generally downward direction along said surface of said evaporation element.

* * * * *